United States Patent
Prasad et al.

(10) Patent No.: US 11,452,742 B2
(45) Date of Patent: Sep. 27, 2022

(54) PHARMACEUTICAL COMPOSITIONS COMPRISING ZINC

(71) Applicants: Zincum, Inc., Addison, TX (US); Wayne State University, Detroit, MI (US)

(72) Inventors: Ananda S. Prasad, Orchard Lake, MI (US); Roy A. Varghese, Garland, TX (US); Kenneth W. Brown, Lewisville, TX (US); Richard P. Scheckenbach, Camas, WA (US)

(73) Assignees: ZINCUM, INC., Addison, TX (US); WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 16/463,113

(22) PCT Filed: Nov. 21, 2017

(86) PCT No.: PCT/US2017/062762
§ 371 (c)(1),
(2) Date: May 22, 2019

(87) PCT Pub. No.: WO2018/098140
PCT Pub. Date: May 31, 2018

(65) Prior Publication Data
US 2020/0061108 A1 Feb. 27, 2020

Related U.S. Application Data

(60) Provisional application No. 62/425,776, filed on Nov. 23, 2016.

(51) Int. Cl.
| | |
|---|---|
| A61K 33/30 | (2006.01) |
| A61K 33/34 | (2006.01) |
| A61K 9/14 | (2006.01) |
| A61K 31/197 | (2006.01) |
| A61K 31/355 | (2006.01) |
| A61K 31/375 | (2006.01) |
| A61K 31/4188 | (2006.01) |
| A61K 31/4415 | (2006.01) |
| A61K 31/455 | (2006.01) |
| A61K 31/519 | (2006.01) |
| A61K 31/714 | (2006.01) |
| A61K 33/04 | (2006.01) |
| A61K 9/16 | (2006.01) |
| A61K 9/48 | (2006.01) |

(52) U.S. Cl.
CPC ............ *A61K 33/30* (2013.01); *A61K 31/197* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/519* (2013.01); *A61K 31/714* (2013.01); *A61K 33/04* (2013.01); *A61K 33/34* (2013.01); *A61K 9/1611* (2013.01); *A61K 9/1652* (2013.01); *A61K 9/4858* (2013.01)

(58) Field of Classification Search
CPC .............. A61K 2300/00; A61K 31/197; A61K 31/355; A61K 31/375; A61K 31/4188; A61K 31/4415; A61K 31/445; A61K 31/519; A61K 31/714; A61K 33/04; A61K 33/30; A61K 33/34; A61K 9/1611; A61K 9/1652; A61K 9/4858; A61P 3/08; A61P 3/10
See application file for complete search history.

(56) References Cited

U.S. PATENT DOCUMENTS

| | | | | |
|---|---|---|---|---|
| 6,630,158 B2* | 10/2003 | Popp | ...................... | A23L 33/00 424/400 |
| 2004/0001817 A1* | 1/2004 | Giampapa | ............ | A61K 36/068 424/94.1 |
| 2013/0323350 A1* | 12/2013 | Seligson | ................. | A23P 10/35 426/2 |
| 2016/0129058 A1* | 5/2016 | Chang | .................... | A61K 31/51 424/93.3 |

OTHER PUBLICATIONS

Tang et al. (J. Nutr. 2001;131:1414-1420). (Year: 2001).*
Zinc; (Mayoclinic [online] retrieved on Sep. 9, 2021 from: https://www.mayoclinic.org/drugs-supplements-zinc/art-20366112; 1 page) (Year : 2021).*

* cited by examiner

*Primary Examiner* — Ernst V Arnold
(74) *Attorney, Agent, or Firm* — Finnegan, Henderson, Farabow, Garrett & Dunner LLP

(57) ABSTRACT

The present disclosure relates to pharmaceutical compositions comprising zinc, copper, at least one micronutrient, and a pharmaceutically acceptable excipient; and comprising administering, to a subject in need thereof, a pharmaceutical composition comprising zinc, copper, at least one micronutrient, and a pharmaceutically acceptable excipient.

20 Claims, No Drawings

PHARMACEUTICAL COMPOSITIONS COMPRISING ZINC

The present application claims the benefit of priority of U.S. Application No. 62/425,776, filed Nov. 23, 2016, which is incorporated herein by reference.

The present disclosure relates to a pharmaceutical composition comprising zinc, copper, at least one micronutrient, and a pharmaceutically acceptable excipient. The present disclosure also relates to methods of increasing phosphorylation of insulin receptor tyrosine kinase, comprising administering, to a subject in need thereof, a pharmaceutical composition according to the present disclosure. The present disclosure further relates to a methods for treating, reducing the severity of, reducing the incidence of, delaying the onset of, or reducing pathogenesis of a chronic condition associated with metabolic syndrome comprising administering, to a subject in need thereof, a pharmaceutical composition according the present disclosure.

Insulin is a hormone produced in the beta islet cells of the pancreas. Insulin plays a significant role in metabolism by aiding in glucose absorption. See, e.g., Saltiel, A. R. and Kahn, C. R. *Nature* 414(6865): 799-806 (2001). After carbohydrates such as sugars and starches are consumed, the human digestive tract breaks down the carbohydrates primarily into glucose. When blood glucose levels rise after consuming a meal, the pancreas releases insulin into the bloodstream. Insulin and glucose are then transported to cells throughout the body, with insulin facilitating cellular intake of glucose and lowering blood glucose levels. In addition, insulin stimulates the liver and muscle tissue to store excess blood glucose. In a healthy individual with abnormal insulin sensitivity, these functions allow both blood glucose and insulin levels to remain in the normal range.

In a person with insulin resistance however, cells do not respond normally to insulin, and cellular uptake of glucose is less efficient. See, e.g., Kahn, B. B. and Flier, J. S. *JCI* 106(4) 473-481 (2000). Because cells do not absorb glucose as efficiently under these conditions, the beta cells in the pancreas usually produce increasing amounts of insulin in an attempt to lower blood glucose levels. In some cases, the pancreas is able to produce enough insulin to overcome the effects of insulin resistance, facilitating sufficient cellular uptake of glucose and maintenance of normal glucose levels.

Over time, however, beta cells in the pancreas fail to keep up with the body's increased need for insulin, and excess glucose accumulates in the bloodstream, leading to higher circulating glucose levels, prediabetes, and other serious health disorders, including accelerated aging. The U.S. Department of Health and Human Services estimated that at least 86 million U.S. adults ages 20 or older in 2012 had prediabetes, a condition in which blood glucose levels are higher than normal but not high enough for a diagnosis of diabetes, and that estimate has risen annually. See the Center for Disease Control's National Diabetes Statistics Report, 2014. In addition to diabetes and prediabetes, insulin resistant individuals are at increased risk of developing dyslipidemia, hypertension, atherosclerosis, endothelial dysfunction, microalbuminuria, obesity, depression, metabolic syndrome, and polycystic ovary syndrome.

Furthermore, glucose-insulin perturbations, particularly insulin resistance, contribute to the increasing prevalence of metabolic syndrome. In non-diabetic individuals, fasting glucose levels correlate significantly in an unhealthful direction with many components of metabolic syndrome. See, e.g., Smyth et al. *Nat Med* 12:75-80 (2005) and Bremer et al. *Pediatrics* 129:557-570 (2012). In fact, with fasting glucose in the non-diabetic range as the independent variable, the following correlations with components of metabolic syndrome are statistically significantly positive: body weight, body fat mass, systolic/diastolic BP, HbA1C, WBC/neutrophil count, and circulating levels of insulin, triglycerides, hsCRP, ALT, and globulins. See Preuss et al. *Original Internist:* 78.

Zinc is the second most abundantly distributed trace element in the body after iron and has many roles, including acting as a cofactor for polymerases and proteases, and acting as an antioxidant. See Saper, R. B., et al. *Am. Fam. Phys.* 2009, vol. 79, 9, pp. 768-72. Because of the ubiquitous nature of zinc, zinc deficiency has been implicated in a number of diseases including diarrhea, age-related macular degeneration, infection, Crohn's Disease, Celiac Disease, sickle cell disease, and the like. See id. Similarly, zinc is known to interfere with copper metabolism and thus is used as a treatment for Wilson's Disease. See Salgueiro, M. J., et al. *Nutr. Res.* 2000, vol. 20, 5, pp. 737-55. Because of the interfering nature of zinc with copper metabolism, copper may be added to a zinc composition in an effort to prevent copper deficiency and disorders related thereto.

Zinc has also been found to be implicated in insulin signaling. For example, when zinc chloride was administered to diabetic rats, hyperglycemia improved. See Rink, L. (Ed.) *Zinc in Human Health*. IOS Press. 2011, vol. 76, p. 498. Further investigation revealed that the zinc led to both stimulation of lipogenesis (formation of fat, in this case from sugar) and oxidation of glucose. See id. Similarly, the zinc supplementation was found to correlate with a lowering of plasma glucose levels and plasma insulin levels. In a separate study, it was demonstrated that use of non-physiological concentrations (i.e., toxically high concentrations) correlated with an increase in protein phosphorylation of the insulin receptor beta subunit in adipocytes and preadipocytes. See id.

The PI3K/Akt signaling pathway is involved in a number of cellular processes, including glucose metabolism. It was demonstrated that exposure of PI3K/Akt kinases to zinc increased signaling, whereas subsequent addition of a PI3K inhibitor led to a decrease in pathway signaling. See id. at p. 499. It is also known that the PI3K/Akt signaling pathway is involved in the insulin signaling pathway, in particular, leading to proliferation and translocation of GLUT4 (glucose transporter 4) into the plasma membrane of a cell, which facilitates glucose uptake.

Taken together, it has been demonstrated that zinc's potential role in protein phosphorylation of the insulin receptor and its potential role in the PI3K/Akt pathway may support the development of zinc supplementation in an effort to maintain insulin function and activity, as well as aiding in the maintenance of healthy levels of blood glucose. Such supplementation may lead to an increased life span, reduced insulin resistance, and a reduced incidence of chronic conditions associated with metabolic syndrome.

In some embodiments, the present disclosure is directed to a pharmaceutical composition comprising zinc, copper, at least one micronutrient, and a pharmaceutically acceptable excipient.

In some embodiments, the zinc is selected from zinc acetate, zinc chloride, zinc sulfate, zinc monomethionine, zinc picolinate, zinc gluconate, zinc aspartate, zinc citrate, zinc orotate, zinc glycinate, zinc oxide, and mixtures thereof. In some embodiments, the zinc is zinc acetate.

In some embodiments, the copper is selected from copper sulfate, copper oxide, copper nitrate, copper citrate, copper glycinate, and mixtures thereof. In some embodiments, the copper is copper sulfate.

In some embodiments, the at least one micronutrient is selected from selenomethionine, L-ascorbic acid, pyridoxine, biotin, vitamin $B_{12}$, folic acid, pantothenic acid, niacin, vitamin E, and mixtures thereof. In some embodiments, the at least one micronutrient is a mixture of selenomethionine, L-ascorbic acid, pyridoxine, biotin, vitamin $B_{12}$, folic acid, pantothenic acid, niacin, and vitamin E. In some embodiments, the at least one micronutrient is a mixture of selenomethionine, L-ascorbic acid, and vitamin E.

In some embodiments, the zinc is present in an amount ranging from about 10 mg to about 100 mg. In some embodiments, the zinc is present in an amount of about 50 mg.

In some embodiments, the copper is present in an amount ranging from about 0.5 mg to about 5 mg. In some embodiments, the copper is present in an amount of about 1.5 mg.

In some embodiments, the selenomethionine is present in an amount ranging from about 25 mcg to about 200 mcg. In some embodiments, the selenomethionine is present in an amount of about 100 mcg.

In some embodiments, the L-ascorbic acid is present in an amount ranging from about 50 mg to about 200 mg. In some embodiments, the L-ascorbic acid is present in an amount of about 120 mg.

In some embodiments, the pyridoxine is present in an amount ranging from about 0.5 mg to about 5 mg. In some embodiments, the pyridoxine is present in an amount of about 2 mg.

In some embodiments, the biotin is present in an amount ranging from about 50 mcg to about 250 mcg. In some embodiments, the biotin is present in an amount of about 150 mcg.

In some embodiments, the vitamin $B_{12}$ is present in an amount ranging from about 50 mcg to about 250 mcg. In some embodiments, the vitamin $B_{12}$ is present in an amount of about 150 mcg.

In some embodiments, the folic acid is present in an amount ranging from about 100 μg to about 700 μg. In some embodiments, the folic acid is present in an amount of about 400 μg.

In some embodiments, the pantothenic acid is present in an amount ranging from about 5 mg to about 15 mg. In some embodiments, the pantothenic acid is present in an amount of about 10 mg.

In some embodiments, the niacin is present in an amount ranging from about 10 mg to about 30 mg. In some embodiments, the niacin is present in an amount of about 20 mg.

In some embodiments, the vitamin E is present in an amount ranging from about 5 IU to about 15 IU. In some embodiments, the vitamin E is present in an amount of about 10 IU.

In some embodiments, provided herein a pharmaceutical composition comprising: about 10 mg to about 100 mg zinc; about 0.5 mg to about 5 mg copper; about 25 mcg to about 200 mcg selenomethionine; about 50 mg to about 200 mg L-ascorbic acid; about 0.5 mg to about 5 mg pyridoxine; about 50 mcg to about 250 mcg biotin; about 50 mcg to about 250 mcg vitamin $B_{12}$; about 100 μg to about 700 μg folic acid; about 5 mg to about 15 mg pantothenic acid; about 10 mg to about 30 mg of niacin; about 5 IU to about 15 IU of vitamin E; and a pharmaceutically acceptable excipient.

In some embodiments, provided herein is a pharmaceutical composition comprising: about 50 mg zinc; about 1.5 mg copper; about 100 mcg selenomethionine; about 120 mg L-ascorbic acid; about 2 mg pyridoxine; about 150 mcg biotin; about 150 mcg vitamin $B_{12}$; about 400 μg folic acid; about 10 mg pantothenic acid; about 20 mg of niacin; about 10 IU of vitamin E; and a pharmaceutically acceptable excipient.

In some embodiments, the zinc is zinc acetate. In some embodiments, the copper is copper sulfate.

In some embodiments, the pharmaceutical composition is formulated as a solid oral dosage form. In some embodiments, the solid oral dosage is a capsule or tablet. In some embodiments, the pharmaceutical composition is formulated as a powder.

In some embodiments, provided herein is a method of increasing phosphorylation of insulin receptor tyrosine kinase, comprising administering, to a subject in need thereof, a pharmaceutical composition according to the present disclosure.

In some embodiments, provided herein is a method for treating, reducing the severity of, reducing the incidence of, delaying the onset of, or reducing pathogenesis of a chronic condition associated with metabolic syndrome comprising administering, to a subject in need thereof, a pharmaceutical composition according to the present disclosure. In some embodiments, the chronic condition is type 2 diabetes.

In some embodiments, provided herein is a method for treating, reducing the severity of, reducing the incidence of, delaying the onset of, or reducing the pathogenesis of insulin resistance comprising administering, to a subject in need thereof, a pharmaceutical composition according to the present disclosure.

In some embodiments, the methods provided herein slows the rate of aging in the subject. In some embodiments, the subject exhibits diabetic fasting glucose levels. In some embodiments, the subject exhibits non-diabetic fasting glucose levels.

In some embodiments, the daily dosage of zinc ranges from about 10 mg to about 100 mg. In some embodiments, the daily dosage of copper ranges from about 0.5 mg to about 5 mg.

In some embodiments, the pharmaceutical composition disclosed herein is administered from one to three times per day. In some embodiments, the pharmaceutical composition disclosed herein is administered one time per day. In some embodiments, the pharmaceutical composition disclosed herein is administered from about 30 minutes to about 8 hours after consumption of food. In some embodiments, the consumption of food is the consumption of a pre-bedtime meal. In some embodiments, the pre-bedtime meal is consumed from about 30 minutes to about 4 hours before bedtime. In some embodiments, the pharmaceutical composition is administered from about 2 hours to about 4 hours after the consumption of a pre-bedtime meal. In some embodiments, the pharmaceutical composition is administered about 3 hours after the consumption of a pre-bedtime meal.

DESCRIPTION

Unless otherwise defined, all technical and scientific terms used herein possess the meaning commonly understood by the skilled artisan. In the case of inconsistencies, the present disclosure, including definitions, controls.

As used above, and throughout the description, the following terms, unless otherwise indicated, shall be understood to have the following meanings:

As used herein, "a" (or "an"), "one or more," and "at least one" can be used interchangeably and refer to one or more of an entity. For example, at least one micronutrient refers to one or more micronutrients.

As used herein, "about" means within 10%, such as within 5% and further such as within 2.5%, of a given value or range. When the term "about" is used in conjunction with a numerical range, it modifies that range by extending the boundaries above and below the numerical values set forth.

As used herein, an "active ingredient" is an ingredient in a pharmaceutical composition that is biologically active (i.e., alters a chemical or physiological function of a cell, tissue, organ, or organism).

As used herein, a "pharmaceutically acceptable excipient" is a functional or non-functional ingredient in a pharmaceutical composition other than the active ingredient(s) useful in preparing said pharmaceutical composition. A "pharmaceutically acceptable excipient" is generally safe and acceptable for mammalian pharmaceutical use.

As used herein, a "disintegrant" is a pharmaceutically acceptable excipient that hydrates a pharmaceutical composition and facilitates the disintegration or breakup of a pharmaceutical composition (e.g., a tablet).

As used herein, a "diluent" or "filler" is an excipient that dilutes the active ingredient(s) and adds bulkiness to a pharmaceutical composition. For example, a diluent or filler may stabilize the active ingredient(s) or facilitate compression.

As used herein, a "surfactant" is an excipient that imparts pharmaceutical compositions with enhanced solubility and/or wettability.

As used herein, a "binder" is a pharmaceutically acceptable excipient that imparts a pharmaceutical composition with cohesive qualities or tensile strength (e.g., hardness).

As used herein, a "glidant" is a pharmaceutically acceptable excipient that imparts a pharmaceutical composition with enhanced flow properties, thereby preventing, reducing, or inhibiting adhesion or friction during processing.

As used herein, a "lubricant" is a pharmaceutically acceptable excipient that imparts improved compaction and ejection properties to a pharmaceutical composition by preventing the active ingredient(s) from clumping together and sticking to manufacturing equipment.

As used herein, "encapsulation machinery" refers to any machine or piece of equipment that may be used to facilitate capsule filling. Encapsulation machinery may be automatic, semiautomatic, or manual.

As used herein, "tableting machinery" refers to any machine or piece of equipment that may be used to facilitate tablet production. Tableting machinery may be automatic, semiautomatic, or manual.

As used herein, an "micronutrient" is an element or substance required in some non-zero amount for the growth and development of living organisms.

As used herein, "% w/w" refers to the weight percentage of an ingredient in a pharmaceutical composition. For example, 5% w/w means that the weight of an ingredient is 5% of the total weight of the pharmaceutical composition. The total weight of the pharmaceutical composition includes the weight of the ingredient.

As used herein, "daily dosage" refers to the total quantity of an active ingredient consumed in the form of a pharmaceutical composition. As used herein, the daily dosage of an active ingredient does not include active ingredient consumed via normal eating behaviors (i.e., dietary sources of the active ingredient).

As used herein, "diabetic fasting glucose levels" refer to blood glucose levels of about 126 mg/dL (7 mmol/L) or higher following at least 8 hours of fasting in which a subject does not eat or drink anything except for water.

As used herein, "non-diabetic fasting glucose levels" refer to blood glucose levels less than about 126 mg/dL (7 mmol/L) following at least 8 hours of fasting in which a subject does not eat or drink anything except for water.

As used herein, "prediabetic fasting glucose levels" refer to blood glucose levels between about 100 mg/dL (5.6 mmol/L) and about 125 mg/dL (6.9 mmol/L) following at least 8 hours of fasting in which a subject does not eat or drink anything except for water.

In one aspect, the present disclosure provides a pharmaceutical composition comprising zinc, copper, at least one micronutrient, and a pharmaceutically acceptable excipient.

In some embodiments, the zinc is selected from zinc acetate, zinc chloride, zinc sulfate, zinc monomethionine, zinc picolinate, zinc gluconate, zinc aspartate, zinc citrate, zinc orotate, zinc glycinate, zinc oxide, and mixtures thereof. In some embodiments, the zinc is zinc acetate. In some embodiments, the zinc is zinc chloride. In some embodiments, the zinc is zinc sulfate. In some embodiments, the zinc is zinc monomethionine. In some embodiments, the zinc is zinc picolinate. In some embodiments, the zinc is zinc gluconate. In some embodiments, the zinc is zinc aspartate. In some embodiments, the zinc is zinc citrate. In some embodiments, the zinc is zinc orotate. In some embodiments, the zinc is zinc glycinate. In some embodiments, the zinc is zinc oxide.

In some embodiments, the copper is selected from copper sulfate, copper oxide, copper nitrate, copper citrate, copper glycinate, and mixtures thereof. In some embodiments, the copper is copper sulfate. In some embodiments, the copper is copper oxide. In some embodiments, the copper is copper nitrate. In some embodiments, the copper is copper citrate. In some embodiments, the copper is copper glycinate.

In some embodiments, the at least one micronutrient is selected from selenomethionine, L-ascorbic acid, pyridoxine, biotin, vitamin $B_{12}$, folic acid, pantothenic acid, niacin, vitamin E, and mixtures thereof. In some embodiments, the at least one micronutrient is selenomethionine. In some embodiments, the at least one micronutrient is L-ascorbic acid. In some embodiments, the at least one micronutrient is pyridoxine. In some embodiments, the at least one micronutrient is biotin. In some embodiments, the at least one micronutrient is vitamin $B_{12}$. In some embodiments, the at least one micronutrient is folic acid. In some embodiments, the at least one micronutrient is pantothenic acid. In some embodiments, the at least one micronutrient is niacin. In some embodiments, the at least one micronutrient is vitamin E. In some embodiments, the at least one micronutrient is a mixture of selenomethionine, L-ascorbic acid, pyridoxine, biotin, vitamin $B_{12}$, folic acid, pantothenic acid, niacin, and vitamin E.

In some embodiments, zinc is present in an amount ranging from about 10 mg to about 100 mg. For example, in some embodiments, zinc is present in an amount of about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. In some embodiments, zinc is present in an amount of about 35 mg. In some embodiments, zinc is present in an amount of about 40 mg. In some embodiments, zinc is present in an amount of about 45 mg. In some embodiments, zinc is present in an amount of about 50 mg. In some embodiments, zinc is present in an amount of about 55 mg.

In some embodiments, copper is present in an amount ranging from about 0.5 mg to about 5 mg. In some embodiments, copper is present in an amount of about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, or about 5 mg. In some embodiments, copper is present in an amount of about 0.75 mg. In some embodiments, copper is present in an amount of about 1 mg. In some embodiments, copper is present in an amount of about 1.25 mg. In some embodiments, copper is present in an amount of about 1.5 mg. In some embodiments, copper is present in an amount of about 1.75 mg. In some embodiments, copper is present in an amount of about 2 mg. In some embodiments, copper is present in an amount of about 2.25 mg.

In some embodiments, selenomethionine is present in an amount ranging from about 25 mcg to about 200 mcg. In some embodiments, selenomethionine is present in amount of about 25 mcg, about 30 mcg, about 35 mcg, about 40 mcg, about 45 mcg, about 50 mcg, about 55 mcg, about 60 mcg, about 65 mcg, about 70 mcg, about 75 mcg, about 80 mcg, about 85 mcg, about 90 mcg, about 95 mcg, about 100 mcg, about 105 mcg, about 110 mcg, about 115 mcg, about 120 mcg, about 125 mcg, about 130 mcg, about 135 mcg, about 140 mcg, about 145 mcg, about 150 mcg, about 155 mcg, about 160 mcg, about 165 mcg, about 170 mcg, about 175 mcg, about 180 mcg, about 185 mcg, about 190 mcg, about 195 mcg or about 200 mcg. In some embodiments, selenomethionine is present in an amount of about 80 mcg. In some embodiments, selenomethionine is present in an amount of about 85 mcg. In some embodiments, selenomethionine is present in an amount of about 90 mcg. In some embodiments, selenomethionine is present in an amount of about 95 mcg. In some embodiments, selenomethionine is present in an amount of about 100 mcg. In some embodiments, selenomethionine is present in an amount of about 105 mcg. In some embodiments, selenomethionine is present in an amount of about 110 mcg. In some embodiments, selenomethionine is present in an amount of about 115 mcg. In some embodiments, selenomethionine is present in an amount of about 120 mcg.

In some embodiments, L-ascorbic acid is present in an amount ranging from about 50 mg to about 200 mg. In some embodiments, L-ascorbic acid is present in an amount of about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, or about 200 mg. In some embodiments, L-ascorbic acid is present in an amount of about 100 mg. In some embodiments, L-ascorbic acid is present in an amount of about 105 mg. In some embodiments, L-ascorbic acid is present in an amount of about 110 mg. In some embodiments, L-ascorbic acid is present in an amount of about 115 mg. In some embodiments, L-ascorbic acid is present in an amount of about 120 mg. In some embodiments, L-ascorbic acid is present in an amount of about 125 mg. In some embodiments, L-ascorbic acid is present in an amount of about 130 mg. In some embodiments, L-ascorbic acid is present in an amount of about 135 mg. In some embodiments, L-ascorbic acid is present in an amount of about 140 mg.

In some embodiments, pyridoxine is present in an amount ranging from about 0.5 mg to about 5 mg. In some embodiments, pyridoxine is present in an amount of about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, or about 5 mg. In some embodiments, pyridoxine is present in an amount of about 1 mg. In some embodiments, pyridoxine is present in an amount of about 1.25 mg. In some embodiments, pyridoxine is present in an amount of about 1.5 mg. In some embodiments, pyridoxine is present in an amount of about 1.75 mg. In some embodiments, pyridoxine is present in an amount of about 2 mg. In some embodiments, pyridoxine is present in an amount of about 2.25 mg. In some embodiments, pyridoxine is present in an amount of about 2.5 mg. In some embodiments, pyridoxine is present in an amount of about 2.75 mg. In some embodiments, pyridoxine is present in an amount of about 3 mg.

In some embodiments, biotin is present in an amount ranging from about 50 mcg to about 250 mcg. In some embodiments, biotin is present in an amount of about 50 mcg, about 75 mcg, about 100 mcg, about 125 mcg, about 150 mcg, about 175 mcg, about 200 mcg, about 225 mcg, or about 250 mcg. In some embodiments, biotin is present in an amount of about 100 mcg. In some embodiments, biotin is present in an amount of about 125 mcg. In some embodiments, biotin is present in an amount of about 150 mcg. In some embodiments, biotin is present in an amount of about 175 mcg. In some embodiments, biotin is present in an amount of about 200 mcg.

In some embodiments, vitamin $B_{12}$ is present in an amount ranging from about 50 mcg to about 250 mcg. In some embodiments, vitamin $B_{12}$ is present in an amount of about 50 mcg, about 75 mcg, about 100 mcg, about 125 mcg, about 150 mcg, about 175 mcg, about 200 mcg, about 225 mcg, or about 250 mcg. In some embodiments, vitamin $B_{12}$ is present in an amount of about 100 mcg. In some embodiments, vitamin $B_{12}$ is present in an amount of about 125 mcg. In some embodiments, vitamin $B_{12}$ is present in an amount of about 150 mcg. In some embodiments, vitamin $B_{12}$ is present in an amount of about 175 mcg. In some embodiments, vitamin $B_{12}$ is present in an amount of about 200 mcg.

In some embodiments, folic acid is present in an amount ranging from about 100 μg to about 800 μg. In some embodiments, folic acid is present in an amount of about 100 μg, about 125 μg, about 150 μg, about 175 μg, about 200 μg, about 225 μg, about 250 μg, about 275 μg, about 300 μg, about 325 μg, about 350 μg, about 375 μg, about 400 μg, about 425 μg, about 450 μg, about 475 μg, about 500 μg, about 525 μg, about 550 μg, about 575 μg, about 600 μg, about 625 μg, about 650 μg, about 675 μg or about 700 μg. In some embodiments, folic acid is present in an amount of about 300 μg. In some embodiments, folic acid is present in an amount of about 325 μg. In some embodiments, folic acid is present in an amount of about 350 μg. In some embodiments, folic acid is present in an amount of about 375 μg. In some embodiments, folic acid is present in an amount of about 400 μg. In some embodiments, folic acid is present in an amount of about 425 μg. In some embodiments, folic acid is present in an amount of about 450 μg. In some embodiments, folic acid is present in an amount of about 475 µg. In some embodiments, folic acid is present in an amount of about 500 µg.

In some embodiments, pantothenic acid is present in an amount of about 5 mg to about 15 mg. In some embodiments, folic acid is present in an amount of about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, or about 15 mg. In some embodiments, pantothenic acid is present in an amount of about 7.5 mg. In some embodiments, pantothenic acid is present in an amount of about 8 mg. In some embodiments, pantothenic acid is present in an amount of about 8.5 mg. In some embodiments, pantothenic acid is present in an amount of about 9 mg. In some embodiments, pantothenic acid is present in an amount of about 9.5 mg. In some embodiments, pantothenic acid is present in an amount of about 10 mg. In some embodiments, pantothenic acid is present in an amount of about 10.5 mg. In some embodiments, pantothenic acid is present in an amount of about 11 mg. In some embodiments, pantothenic acid is present in an amount of about 11.5 mg. In some embodiments, pantothenic acid is present in an amount of about 12 mg. In some embodiments, pantothenic acid is present in an amount of about 12.5 mg.

In some embodiments, niacin is present in an amount ranging from about 10 mg to about 30 mg. In some embodiments, niacin is present in an amount of about 10 mg, about 12.5 mg, about 15 mg, about 17.5 mg, about 20 mg, about 22.5 mg, about 25 mg, about 27.5 mg, or about 30 mg. In some embodiments, niacin is present in an amount of about 15 mg. In some embodiments, niacin is present in an amount of about 17.5 mg. In some embodiments, niacin is present in an amount of about 20 mg. In some embodiments, niacin is present in an amount of about 22.5 mg. In some embodiments, niacin is present in an amount of about 25 mg.

In some embodiments, vitamin E is present in an amount ranging from about 5 IU to about 15 IU. In some embodiments, vitamin E is present in an amount of about 5 IU, about 5.5 IU, about 6 IU, about 6.5 IU, about 7 IU, about 7.5 IU, about 8 IU, about 8.5 IU, about 9 IU, about 9.5 IU, about 10 IU, about 10.5 IU, about 11 IU, about 11.5 IU, about 12 IU, about 12.5 IU, about 13 IU, about 13.5 IU, about 14 IU, about 14.5 IU, or about 15 IU. In some embodiments, vitamin E is present in an amount of about 7.5 IU. In some embodiments, vitamin E is present in an amount of about 8 IU. In some embodiments, vitamin E is present in an amount of about 8.5 IU. In some embodiments, vitamin E is present in an amount of about 9 IU. In some embodiments, vitamin E is present in an amount of about 9.5 IU. In some embodiments, vitamin E is present in an amount of about 10 IU. In some embodiments, vitamin E is present in an amount of about 10.5 IU. In some embodiments, vitamin E is present in an amount of about 11 IU. In some embodiments, vitamin E is present in an amount of about 11.5 IU. In some embodiments, vitamin E is present in an amount of about 11.5 IU. In some embodiments, vitamin E is present in an amount of about 12 IU. In some embodiments, vitamin E is present in an amount of about 12.5 IU.

In another aspect, the present disclosure provides a pharmaceutical composition of claim 1 comprising:
about 10 mg to about 100 mg zinc;
about 0.5 mg to about 5 mg copper;
about 25 mcg to about 200 mcg selenomethionine;
about 50 mg to about 200 mg L-ascorbic acid;
about 0.5 mg to about 5 mg pyridoxine;
about 50 mcg to about 250 mcg biotin;
about 50 mcg to about 250 mcg vitamin $B_{12}$;
about 100 µg to about 700 µg folic acid;
about 5 mg to about 15 mg pantothenic acid;
about 10 mg to about 30 mg of niacin;
about 5 IU to about 15 IU of vitamin E; and
a pharmaceutically acceptable excipient.

In some embodiments, the pharmaceutical composition comprises:
about 50 mg zinc;
about 1.5 mg copper;
about 100 mcg selenomethionine;
about 120 mg L-ascorbic acid;
about 2 mg pyridoxine;
about 150 mcg biotin;
about 150 mcg vitamin $B_{12}$;
about 400 µg folic acid;
about 10 mg pantothenic acid;
about 20 mg of niacin;
about 10 IU of vitamin E; and
a pharmaceutically acceptable excipient.

In some embodiments, the total weight percentage of pharmaceutical excipient(s) in a pharmaceutical composition disclosed herein is up to about 35% w/w. For example, in some embodiments, the total weight percentage of pharmaceutical excipient(s) in a pharmaceutical composition disclosed herein is up to about 35% w/w, up to about 30% w/w, up to about 25% w/w, up to about 20% w/w, up to about 15% w/w, or up to about 10% w/w.

In some embodiments, a pharmaceutical composition disclosed herein is formulated as a solid oral dosage form. Non-limiting examples of solid oral dosage forms include tablets, such as a sugar-coated tablet, a film-coated tablet, a sublingual tablet, a buccal tablet, or an orally disintegrating oral tablet, and capsules, such as a soft capsule or microcapsule.

A pharmaceutical composition of the present disclosure may be produced by compacting or compressing an admixture or composition, for example, a powder or granules, under pressure to form a stable three-dimensional shape such a tablet. A solid oral dosage form of the disclosure may possess almost any shape including concave and/or convex faces, rounded or angled corners, and a rounded to rectilinear shape. In some embodiments, the solid oral dosage form may be a rounded tablet having flat faces.

In some embodiments, the solid oral dosage form is a capsule. In some embodiments, the solid oral dosage form is a hard capsule. In some embodiments, the solid oral dosage form is a soft gel capsule. The pharmaceutical composition in any capsule compartment may be present in any suitable form, e.g., as a powder, granules, compacts, or microcapsules. The contents of the compartments, e.g., drug substances, may be introduced into the compartments by standard methods used conventionally for filling capsules. The capsule material may be selected from materials acceptable for the delivery of a pharmaceutical or food composition. Non-limiting examples of suitable capsule materials are gelatin and plant based polymers.

A solid oral dosage form of the present disclosure may be prepared by any known production method generally used in the technical field of pharmaceuticals preparation. In particular embodiments, solid oral dosage forms provided herein may be prepared using conventional methods known to those skilled in the field of pharmaceutical preparation, as described, e.g., in pertinent textbooks. See, e.g., Remington: The Science and Practice of Pharmacy, 21st Ed., Lippincott Williams & Wilkins, Baltimore, Md. (2003); Ansel et al., Pharmaceutical Dosage Forms And Drug Delivery Systems, 7th Edition, Lippincott Williams & Wilkins, (1999); The Handbook of Pharmaceutical Excipients, 4th edition, Rowe et al., Eds., American Pharmaceuticals Association (2003); Gibson, Pharmaceutical Preformulation And Formulation, CRC Press (2001). These references are hereby incorporated herein by reference to the extent they disclose suitable, conventional methods known to those skilled in the field of pharmaceutical formulation.

A pharmaceutical composition of the present disclosure comprises a pharmaceutically acceptable excipient. Non-limiting examples of a pharmaceutically acceptable excipient include binders, disintegrants, fillers, glidants, lubricants, preservatives, antifoaming agents, fillers, colorants, lubricants, and plasticizers. Pharmaceutically acceptable excipients are well-known in the art, see, e.g., Remington: The Science and Practice of Pharmacy, Twenty-first Ed., (Pharmaceutical Press, 2005); Liberman, H. A., Lachman, L., and Schwartz, J. B. Eds., Pharmaceutical Dosage Forms, Vol. 1-2 Taylor & Francis 1990; and R. I. Mahato, Ansel's Pharmaceutical Dosage Forms and Drug Delivery Systems, Second Ed. (Taylor & Francis, 2012), which is incorporated by reference to the extent it discloses lists of pharmaceutically acceptable excipients. Using methods generally used in the technical field of pharmaceutical preparations, the skilled artisan would know how to evaluate the compatibility of excipients with the active ingredients, i.e., zinc, copper, and at least one micronutrient, of the pharmaceutical composition.

In some embodiments, a pharmaceutical composition of the present disclosure comprises filler, a binder, a disintegrant, a lubricant, or a glidant. In some embodiments, the filler is mannitol, sorbitol, gelatin, dibasic calcium phosphate dihydrate, dibasic calcium phosphate anhydrate, and tribasic calcium phosphate, or any mixture thereof. In some embodiments, the binder is hydroxypropyl cellulose, alginic acid, carboxymethylcellulose sodium, copovidone, methylcellulose, or any mixture thereof. In some embodiments, the disintegrant is sodium starch glycolate, croscarmellose sodium, crospovidone, or any mixture thereof. In some embodiments, the lubricant is magnesium stearate, stearic acid, palmitic acid, calcium stearate, carnauba wax, hydrogenated vegetable oils, mineral oil, polyethylene glycols, or sodium stearyl fumarate. In some embodiments, the glidant is colloidal silicon dioxide.

In some embodiments, the pharmaceutically acceptable excipient comprises a filler, a disintegrant, a lubricant, and a glidant. In some embodiments, the filler is gelatin. In some embodiments, the disintegrant is microcrystalline cellulose. In some embodiments, the lubricant is magnesium stearate. In some embodiments, the glidant is silicon dioxide.

In some embodiments, the pharmaceutically acceptable excipient comprises a preservative. Non-limiting examples of preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, the pharmaceutically acceptable excipient comprises a disintegrant. Non-limiting examples of disintegrants include a starch, e.g., a natural starch such as corn starch or potato starch, a pregelatinized starch such as National 1551 or sodium starch glycolate such as Promogel® or Explotab®, a cellulose such as a wood product, methylcrystalline cellulose, e.g., Avicel®, Avicel® PH101, Avicel® PH 102, Avicel® PH105, Elceme® P100, Emcocel®, Vivacel®, and Solka-Floc®, methylcellulose, croscarmellose, or a cross-linked cellulose, such as cross-linked sodium carboxymethyl-cellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and mixtures thereof.

In certain embodiments, the pharmaceutically acceptable excipient comprises a diluent. Non-limiting examples of diluents include lactose, gelatin, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); hydroxypropyl-methylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and mixtures thereof.

In some embodiments, a pharmaceutical composition disclosed herein is formulated as one, two, or three solid oral dosage forms. In some embodiments, a pharmaceutical composition disclosed herein is formulated as one solid oral dosage forms. In some embodiments, a pharmaceutical composition disclosed herein is formulated as two solid oral dosage forms. In some embodiments, a pharmaceutical composition disclosed herein is formulated as three solid oral dosage forms.

In some embodiments, the pharmaceutical compositions disclosed herein are formulated as a powder.

In some embodiments, the pharmaceutical composition disclosed herein may be formulated as a liquid.

In another aspect, the present disclosure provides a method for producing a capsule comprising zinc, copper, at least one micronutrient, and a pharmaceutically acceptable excipient, comprising the steps of:

blending zinc, copper, the at least one micronutrient, and the pharmaceutically acceptable excipient(s) into a homogeneous powder; and transferring the powder to encapsulating machinery, and filling the capsule using the encapsulating machinery.

In some embodiments, the encapsulating machinery is automatic, semi-automatic, or manual. Non-limiting examples of encapsulating machinery include LIQFIL super Labo Capsule Filling Machine by Qualicaps and Capsugel Ultra 8 II.

In some embodiments, the method further comprises one or more of the following steps prior to blending zinc, copper, the at least one micronutrient, and the pharmaceutically acceptable excipient(s) into a homogeneous powder:

analyzing a physical characteristic of one or more of zinc, copper, the at least one micronutrient, or the pharmaceutically acceptable excipient(s);

hygienic analysis of one or more of zinc, copper, the at least one micronutrient, or the pharmaceutically acceptable excipient(s);

purity and potency analysis of one or more of zinc, copper, the at least one micronutrient, or the pharmaceutically acceptable excipient(s).

Non-limiting examples of methods for analyzing physical characteristics include organoleptic analyses and particle size analysis.

Non-limiting examples of methods for hygienic analysis include total plate counts for microorganisms (e.g., *Escherichia coli, Staphylococcus aureus*, or yeast), wherein one or more of the zinc, copper, at least one micronutrient, or the pharmaceutically acceptable excipient(s) is added to a sterile plate with solid growth medium and growth of microorganisms on the plate is measured over time relative to a control plate.

Non-limiting examples of methods for purity and potency analysis include high performance liquid chromatography and atomic absorption.

In some embodiments, the ambient temperature is below about 90° F. In some embodiments, the encapsulating machinery temperature is below about 90° F. In some embodiments, the ambient temperature and the encapsulating machinery temperature is below about 90° F.

In another aspect, the present disclosure provides a method for producing a tablet comprising zinc, copper, at least one micronutrient, and a pharmaceutically acceptable excipient, comprising the steps of:

blending zinc, copper, the at least one micronutrient, and the pharmaceutically acceptable excipient(s) into a homogeneous powder;

transferring the powder to tableting machinery; and compressing the powder using the tableting machinery.

In some embodiments, the method further comprises the steps of:

transferring the compressed powder to a coating pan; and coating the tablet.

In some embodiments, the method further comprises one or more of the following steps prior to blending zinc, copper, the at least one micronutrient, and the pharmaceutically acceptable excipient(s) into a homogeneous powder:

analyzing a physical characteristic of one or more of zinc, copper, the at least one micronutrient, or the pharmaceutically acceptable excipient(s);

hygienic analysis of one or more of zinc, copper, the at least one micronutrient, or the pharmaceutically acceptable excipient(s);

purity and potency analysis of one or more of zinc, copper, the at least one micronutrient, or the pharmaceutically acceptable excipient(s).

In one aspect, the present disclosure provides a method of increasing phosphorylation of insulin receptor tyrosine kinase comprising administering, to a subject in need thereof, a pharmaceutical composition disclosed herein.

In some embodiments, said method results in lower blood sugar levels. In some embodiments, said method results in more consistent blood sugar levels. In some embodiments, said method reduces the severity or frequency of blood sugar spikes.

In another aspect, the present disclosure provides a method for treating, reducing the severity of, reducing the incidence of, delaying the onset of, or reducing pathogenesis of a chronic condition associated with metabolic syndrome comprising administering, to a subject in need thereof, a pharmaceutical composition described herein. In some embodiments, disclosed herein is a method for treating a chronic condition associated with metabolic syndrome comprising administering, to a subject in need thereof, a pharmaceutical composition described herein. In some embodiments, disclosed herein is a method for reducing the severity of a chronic condition associated with metabolic syndrome comprising administering, to a subject in need thereof, a pharmaceutical composition described herein. In some embodiments, disclosed herein is a method for reducing the incidence of a chronic condition associated with metabolic syndrome comprising administering, to a subject in need thereof, a pharmaceutical composition described herein. In some embodiments, disclosed herein is a method for delaying the onset of a chronic condition associated with metabolic syndrome comprising administering, to a subject in need thereof, a pharmaceutical composition described herein. In some embodiments, disclosed herein is a method for reducing pathogenesis of a chronic condition associated with metabolic syndrome comprising administering, to a subject in need thereof, a pharmaceutical composition described herein.

In some embodiments, the chronic condition associated with metabolic syndrome is selected from insulin resistance, prediabetes, type 2 diabetes, obesity, nonalcoholic fatty liver disease, chronic kidney disease, elevated blood pressure, polycystic ovary syndrome, cardiovascular disorders such as hypertension, and dyslipidemias such as high triglyceride and low HDL-cholesterol levels, acanthosis nigricans, hirsutism, peripheral neuropathy, and retinopathy.

In some embodiments, the chronic condition associated with metabolic syndrome is insulin resistance. In some embodiments, the chronic condition associated with metabolic syndrome is prediabetes. In some embodiments, the chronic condition associated with metabolic syndrome is type 2 diabetes. In some embodiments, the condition associated with metabolic syndrome is obesity. In some embodiments, the condition associated with metabolic syndrome is nonalcoholic fatty liver disease. In some embodiments, the condition associated with metabolic syndrome is chronic kidney disease. In some embodiments, the chronic condition associated with metabolic syndrome is elevated blood pressure. In some embodiments, the chronic condition associated with metabolic syndrome is high blood pressure. In some embodiments, the condition associated with metabolic syndrome is polycystic ovary syndrome. In some embodiments, the condition associated with metabolic syndrome is cardiovascular disorder.

In some embodiments, the cardiovascular disorder is selected from hypertension and dyslipidemias (e.g., high triglyceride and low HDL-cholesterol levels), acanthosis nigricans, hirsutism, peripheral neuropathy, and retinopathy.

In another aspect, the present disclosure provides a method for treating, reducing the severity of, reducing the incidence of, delaying the onset of, or reducing pathogenesis of insulin resistance comprising administering, to a subject in need thereof, a pharmaceutical composition described herein.

In some embodiments, provided herein is a method of treating insulin resistance comprising administering, to a subject in need thereof, a pharmaceutical composition described herein. In some embodiments, provided herein is a method for reducing the severity of insulin resistance comprising administering, to a subject in need thereof, a pharmaceutical composition described herein. In some embodiments, provided herein is a method for reducing the incidence of insulin resistance comprising administering, to a subject in need thereof, a pharmaceutical composition described herein. In some embodiments, provided herein is a method for delaying the onset of insulin resistance comprising administering, to a subject in need thereof, a pharmaceutical composition described herein. In some embodiments, provided herein is a method for reducing pathogenesis of insulin resistance comprising administering, to a subject in need thereof, a pharmaceutical composition described herein.

In some embodiments, the method further comprising slowing the rate of aging in the subject in need thereof.

In some embodiments, the daily dose of zinc ranges from about 10 mg to about 100 mg. For example, in some embodiments, the daily dose of zinc is about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg. In some embodiments, the daily dose of zinc is about 35 mg. In some embodiments, the daily dose of zinc is about 40 mg. In some embodiments, the daily dose of zinc is about 45 mg. In some embodiments, the daily dose of zinc is about 50 mg. In some embodiments, the daily dose of zinc is about 55 mg.

In some embodiments, the daily dose of copper is ranges from about 0.5 mg to about 5 mg. In some embodiments, the daily dose of copper is about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, or about 5 mg. In some embodiments, the daily dose of copper is about 0.75 mg. In some embodiments, the daily dose of copper is about 1 mg. In some embodiments, the daily dose of copper is about 1.25 mg. In some embodiments, the daily dose of copper is about 1.5 mg. In some embodiments, the daily dose of copper is about 1.75 mg. In some embodiments, the daily dose of copper is about 2 mg. In some embodiments, the daily dose of copper is about 2.25 mg.

In some embodiments, the daily dose of selenomethionine ranges from about 25 mcg to about 200 mcg. In some embodiments, the daily dose of selenomethionine is about 25 mcg, about 30 mcg, about 35 mcg, about 40 mcg, about 45 mcg, about 50 mcg, about 55 mcg, about 60 mcg, about 65 mcg, about 70 mcg, about 75 mcg, about 80 mcg, about 85 mcg, about 90 mcg, about 95 mcg, about 100 mcg, about 105 mcg, about 110 mcg, about 115 mcg, about 120 mcg, about 125 mcg, about 130 mcg, about 135 mcg, about 140 mcg, about 145 mcg, about 150 mcg, about 155 mcg, about 160 mcg, about 165 mcg, about 170 mcg, about 175 mcg, about 180 mcg, about 185 mcg, about 190 mcg, about 195 mcg or about 200 mcg. In some embodiments, the daily dose of selenomethionine is about 80 mcg. In some embodiments, the daily dose of selenomethionine is about 85 mcg. In some embodiments, the daily dose of selenomethionine is about 90 mcg. In some embodiments, the daily dose of selenomethionine is about 95 mcg. In some embodiments, the daily dose of selenomethionine is about 100 mcg. In some embodiments, the daily dose of selenomethionine is about 105 mcg. In some embodiments, the daily dose of selenomethionine is about 110 mcg. In some embodiments, the daily dose of selenomethionine is about 115 mcg. In some embodiments, the daily dose of selenomethionine is about 120 mcg.

In some embodiments, the daily dose of L-ascorbic acid ranges from about 50 mg to about 200 mg. In some embodiments, the daily dose of L-ascorbic acid is about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, or about 200 mg. In some embodiments, the daily dose of L-ascorbic acid is about 100 mg. In some embodiments, the daily dose of L-ascorbic acid is about 105 mg. In some embodiments, the daily dose of L-ascorbic acid is about 110 mg. In some embodiments, the daily dose of L-ascorbic acid is about 115 mg. In some embodiments, the daily dose of L-ascorbic acid is about 120 mg. In some embodiments, the daily dose of L-ascorbic acid is about 125 mg. In some embodiments, the daily dose of L-ascorbic acid is about 130 mg. In some embodiments, the daily dose of L-ascorbic acid is about 135 mg. In some embodiments, the daily dose of L-ascorbic acid is about 140 mg.

In some embodiments, the daily dose of pyridoxine ranges from about 0.5 mg to about 5 mg. In some embodiments, the daily dose of pyridoxine is about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, or about 5 mg. In some embodiments, the daily dose of pyridoxine is about 1 mg. In some embodiments, the daily dose of pyridoxine is about 1.25 mg. In some embodiments, the daily dose of pyridoxine is about 1.5 mg. In some embodiments, the daily dose of pyridoxine is about 1.75 mg. In some embodiments, the daily dose of pyridoxine is about 2 mg. In some embodiments, the daily dose of pyridoxine is about 2.25 mg. In some embodiments, the daily dose of pyridoxine is about 2.5 mg. In some embodiments, the daily dose of pyridoxine is about 2.75 mg. In some embodiments, the daily dose of pyridoxine is about 3 mg.

In some embodiments, the daily dose of biotin ranges from about 50 mcg to about 250 mcg. In some embodiments, the daily dose of biotin is about 50 mcg, about 75 mcg, about 100 mcg, about 125 mcg, about 150 mcg, about 175 mcg, about 200 mcg, about 225 mcg, or about 250 mcg. In some embodiments, the daily dose of biotin is about 100 mcg. In some embodiments, the daily dose of biotin is about 125 mcg. In some embodiments, the daily dose of biotin is about 150 mcg. In some embodiments, the daily dose of biotin is about 175 mcg. In some embodiments, the daily dose of biotin is about 200 mcg.

In some embodiments, the daily dose of vitamin $B_{12}$ ranges from about 50 mcg to about 250 mcg. In some embodiments, the daily dose of vitamin $B_{12}$ is about 50 mcg, about 75 mcg, about 100 mcg, about 125 mcg, about 150 mcg, about 175 mcg, about 200 mcg, about 225 mcg, or about 250 mcg. In some embodiments, the daily dose of vitamin $B_{12}$ is about 100 mcg. In some embodiments, the daily dose of vitamin $B_{12}$ is about 125 mcg. In some embodiments, the daily dose of vitamin $B_{12}$ is about 150 mcg. In some embodiments, the daily dose of vitamin $B_{12}$ is about 175 mcg. In some embodiments, the daily dose of vitamin $B_{12}$ is about 200 mcg.

In some embodiments, the daily dose of folic acid ranges from about 100 μg to about 800 μg. In some embodiments, the daily dose of folic acid is about 100 μg, about 125 μg, about 150 μg, about 175 μg, about 200 μg, about 225 μg, about 250 μg, about 275 μg, about 300 μg, about 325 μg, about 350 μg, about 375 μg, about 400 μg, about 425 μg, about 450 μg, about 475 μg, about 500 μg, about 525 μg, about 550 μg, about 575 μg, about 600 μg, about 625 μg, about 650 μg, about 675 μg or about 700 μg. In some embodiments, the daily dose of folic acid is about 300 μg. In some embodiments, the daily dose of folic acid is about 325 μg. In some embodiments, the daily dose of folic acid is about 350 μg. In some embodiments, the daily dose of folic acid is about 375 µg. In some embodiments, the daily dose of folic acid is about 400 µg. In some embodiments, the daily dose of folic acid is about 425 µg. In some embodiments, the daily dose of folic acid is about 450 µg. In some embodiments, the daily dose of folic acid is about 475 µg. In some embodiments, the daily dose of folic acid is about 500 µg.

In some embodiments, the daily dose of pantothenic acid ranges from about 5 mg to about 15 mg. In some embodiments, the daily dose of folic acid is about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 11.5 mg, about 12 mg, about 12.5 mg, about 13 mg, about 13.5 mg, about 14 mg, about 14.5 mg, or about 15 mg. In some embodiments, the daily dose of pantothenic acid is about 7.5 mg. In some embodiments, the daily dose of pantothenic acid is about 8 mg. In some embodiments, the daily dose of pantothenic acid is about 8.5 mg. In some embodiments, the daily dose of pantothenic acid is about 9 mg. In some embodiments, the daily dose of pantothenic acid is about 9.5 mg. In some embodiments, the daily dose of pantothenic acid is about 10 mg. In some embodiments, the daily dose of pantothenic acid is about 10.5 mg. In some embodiments, the daily dose of pantothenic acid is about 11 mg. In some embodiments, the daily dose of pantothenic acid is about 11.5 mg. In some embodiments, the daily dose of pantothenic acid is about 12 mg. In some embodiments, the daily dose of pantothenic acid is about 12.5 mg.

In some embodiments, the daily dose of niacin ranges from about 10 mg to about 30 mg. In some embodiments, the daily dose of niacin is about 10 mg, about 12.5 mg, about 15 mg, about 17.5 mg, about 20 mg, about 22.5 mg, about 25 mg, about 27.5 mg, or about 30 mg. In some embodiments, the daily dose of niacin is about 15 mg. In some embodiments, the daily dose of niacin is about 17.5 mg. In some embodiments, the daily dose of niacin is about 20 mg. In some embodiments, the daily dose of niacin is about 22.5 mg. In some embodiments, the daily dose of niacin is about 25 mg.

In some embodiments, the daily dose of vitamin E ranges from about 5 IU to about 15 IU. In some embodiments, the daily dose of vitamin E is about 5 IU, about 5.5 IU, about 6 IU, about 6.5 IU, about 7 IU, about 7.5 IU, about 8 IU, about 8.5 IU, about 9 IU, about 9.5 IU, about 10 IU, about 10.5 IU, about 11 IU, about 11.5 IU, about 12 IU, about 12.5 IU, about 13 IU, about 13.5 IU, about 14 IU, about 14.5 IU, or about 15 IU. In some embodiments, the daily dose of vitamin E is about 7.5 IU. In some embodiments, the daily dose of vitamin E is about 8 IU. In some embodiments, the daily dose of vitamin E is about 8.5 IU. In some embodiments, the daily dose of vitamin E is about 9 IU. In some embodiments, the daily dose of vitamin E is about 9.5 IU. In some embodiments, the daily dose of vitamin E is about 10 IU. In some embodiments, the daily dose of vitamin E is about 10.5 IU. In some embodiments, the daily dose of vitamin E is about 11 IU. In some embodiments, the daily dose of vitamin E is about 11.5 IU. In some embodiments, the daily dose of vitamin E is about 11.5 IU. In some embodiments, the daily dose of vitamin E is about 12 IU. In some embodiments, the daily dose of vitamin E is about 12.5 IU.

In some embodiments, the pharmaceutical composition described herein is administered from one to three times per day. In some embodiments, the pharmaceutical composition described herein is administered one time per day. In some embodiments, the pharmaceutical composition described herein is administered two timers per day. In some embodiments, the pharmaceutical composition is administered three times per day.

In some embodiments, the pharmaceutical composition described herein is administered at a time ranging from about 30 minutes to about 8 hours after the consumption of food. In some embodiments, the consumption of food is the consumption of a pre-bedtime meal. In some embodiments, the pre-bedtime meal is consumed about 30 minutes to about 4 hours before bedtime. In some embodiments, the pharmaceutical composition described herein is administered about 2 hours to about 4 hours after the consumption of a pre-bedtime meal. In some embodiments, the pharmaceutical composition described herein is administered about 3 hours after the consumption of a pre-bedtime meal.

In some embodiments of all aspects, the subject in need thereof has pre-diabetic fasting blood glucose levels. In some other embodiments, the subject in need thereof has diabetic fasting blood glucose levels.

In some embodiments of all aspects, the subject in need thereof has insulin resistance.

In some embodiments of all aspects, the subject in need thereof has metabolic syndrome.

In some embodiments of all aspects, the subject in need thereof has type 2 diabetes or prediabetes.

EXAMPLES

Example 1: Administration

A subject with type 2 diabetes may lower his or her blood sugar level and support insulin function and activity by taking one capsule, one time per day, about three hours after their pre-bedtime meal, wherein the capsule comprises:
about 50 mg zinc acetate;
about 1.5 mg copper sulfate;
about 100 mcg selenomethionine;
about 120 mg L-ascorbic acid;
about 2 mg pyridoxine;
about 150 mcg biotin;
about 150 mcg vitamin $B_{12}$;
about 400 µg folic acid;
about 10 mg pantothenic acid;
about 20 mg of niacin; and
about 10 IU of vitamin E.

Regardless of demography, the subject may take the capsule after his or her pre-bedtime meal. The exact time of capsule administration may vary from about 2 hours to about 4 hours after the consumption of a pre-bedtime meal.

In some instances, subjects suffering from acute infections, liver disease, cancer, renal insufficiency, and/or having had surgery within the past three months may be advised to not ingest such capsule.

In some embodiments, parameters such as blood chemistry, weight, weight loss, appetite, oxidative stress, cell mediated immune functions, and inflammatory cytokines will be monitored.

Example 2: Capsule Manufacturing

A capsule comprising zinc acetate, copper sulfate or copper oxide, selenomethionine, L-ascorbic acid, pyridoxine, biotin, vitamin $B_{12}$, folic acid, panthothenic acid, niacin, and vitamin E may be prepared by obtaining zinc acetate, copper sulfate or copper oxide, selenomethionine, L-ascorbic acid, pyridoxine, biotin, vitamin $B_{12}$, folic acid, panthothenic acid, niacin, and vitamin E in powder form from commercial suppliers. The active ingredients may be analyzed to evaluate quality/purity. Non-limiting analysis examples include physical characteristics analysis (e.g., organoleptic analyses and particle size analysis), hygienic analysis (e.g., total plate count for microorganisms), and purity and potency analysis (e.g., HPLC, atomic absorption, and other analytical techniques). After analysis, the active ingredients are weighed, double-checked for proper amounts, and blended with pharmaceutically acceptable excipients until the powder mix is homogeneous. Non-limiting examples of pharmaceutically acceptable excipients include microcrystalline cellulose, magnesium stearate, and silicon dioxide. The powder is transferred to encapsulating machinery, and gelatin capsules are filled with said powder, dusted, polished, and check-weighed. Sample capsules are randomly selected and analyzed for specific nutrients or related ingredients, as well as for meeting quality and safety standards.

While the foregoing disclosure has been described in some detail for purposes of clarity and understanding, the disclosure is to be considered as illustrative and not restrictive. The skilled artisan reading this disclosure will appreciate that various changes in form and detail can be made without departing from the scope of the disclosure.

What is claimed is:

1. A method of increasing phosphorylation of insulin receptor tyrosine kinase, comprising administering, to a subject in need thereof, a pharmaceutical composition consisting of zinc; copper; selenomethionine; at least one micronutrient chosen from the group consisting of L-ascorbic acid, pyridoxine, biotin, vitamin B12, folic acid, pantothenic acid, niacin, and vitamin E; and a pharmaceutically acceptable excipient; wherein the zinc is present in the pharmaceutical composition in an amount of about 45 mg to about 100 mg.

2. The method of increasing phosphorylation of insulin receptor tyrosine kinase according to claim 1, wherein the zinc is selected from zinc acetate, zinc chloride, zinc sulfate, zinc monomethionine, zinc picolinate, zinc gluconate, zinc aspartate, zinc citrate, zinc orotate, zinc glycinate, zinc oxide, and mixtures thereof.

3. The method of increasing phosphorylation of insulin receptor tyrosine kinase according to claim 2, wherein the zinc is present in the pharmaceutical composition in an amount of about 50 mg.

4. The method of increasing phosphorylation of insulin receptor tyrosine kinase according to claim 1, wherein the zinc is zinc acetate.

5. The method of increasing phosphorylation of insulin receptor tyrosine kinase according to claim 4, wherein the at least one micronutrient is a mixture of L-ascorbic acid, pyridoxine, biotin, vitamin B12, folic acid, pantothenic acid, niacin, and vitamin E.

6. The method of increasing phosphorylation of insulin receptor tyrosine kinase according to claim 4, wherein the at least one micronutrient is a mixture of L-ascorbic acid and vitamin E.

7. The method of increasing phosphorylation of insulin receptor tyrosine kinase according to claim 5, wherein the vitamin B12 is present in the pharmaceutical composition in an amount of about 150 mcg.

8. The method of increasing phosphorylation of insulin receptor tyrosine kinase according to claim 1, wherein the pharmaceutical composition consists of:
    about 45 mg to about 100 mg zinc;
    about 0.5 mg to about 5 mg copper;
    about 25 mcg to about 200 mcg selenomethionine;
    about 50 mg to about 200 mg L-ascorbic acid;
    about 0.5 mg to about 5 mg pyridoxine;
    about 50 mcg to about 250 mcg biotin;
    about 50 mcg to about 250 mcg vitamin B12;
    about 100 µg to about 700 µg folic acid;
    about 5 mg to about 15 mg pantothenic acid;
    about 10 mg to about 30 mg niacin;
    about 5 IU to about 15 IU vitamin E; and
    a pharmaceutically acceptable excipient.

9. The method of increasing phosphorylation of insulin receptor tyrosine kinase according to claim 8, wherein the pharmaceutical composition consists of:
    about 50 mg zinc;
    about 1.5 mg copper;
    about 100 mcg selenomethionine;
    about 120 mg L-ascorbic acid;
    about 2 mg pyridoxine;
    about 150 mcg biotin;
    about 150 mcg vitamin B12;
    about 400 µg folic acid;
    about 10 mg pantothenic acid;
    about 20 mg niacin;
    about 10 IU vitamin E; and
    a pharmaceutically acceptable excipient.

10. The method of increasing phosphorylation of insulin receptor tyrosine kinase according to claim 8 or 9, wherein the zinc is zinc acetate.

11. The method of increasing phosphorylation of insulin receptor tyrosine kinase according to claim 8 or 9, wherein the copper is copper sulfate.

12. The method of increasing phosphorylation of insulin receptor tyrosine kinase according to any one of claims 2, 5, 6, 3, 7, 8, and 9, wherein the pharmaceutical composition is formulated as a powder.

13. The method of increasing phosphorylation of insulin receptor tyrosine kinase according to claim 1, wherein the pharmaceutical composition is administered from one to three times per day.

14. The method of increasing phosphorylation of insulin receptor tyrosine kinase according to claim 1, wherein the pharmaceutical composition is administered from about 30 minutes to about 8 hours after consumption of food.

15. The method of increasing phosphorylation of insulin receptor tyrosine kinase according to claim 14, wherein the consumption of food is the consumption of a pre-bedtime meal.

16. The method of increasing phosphorylation of insulin receptor tyrosine kinase according to claim 1, wherein the pharmaceutical composition is administered about 2 hours after consumption of food.

17. A method for treating, reducing the severity of, reducing the incidence of, delaying the onset of, or reducing the pathogenesis of insulin resistance in a subject in need thereof, comprising administering to the subject a pharmaceutical composition consisting of:
    about 45 mg to about 100 mg zinc;
    about 0.5 mg to about 5 mg copper;
    about 25 mcg to about 200 mcg selenomethionine;
    about 50 mg to about 200 mg L-ascorbic acid;
    about 0.5 mg to about 5 mg pyridoxine;
    about 50 mcg to about 250 mcg biotin;
    about 50 mcg to about 250 mcg vitamin B12;
    about 100 µg to about 700 µg folic acid;
    about 5 mg to about 15 mg pantothenic acid;
    about 10 mg to about 30 mg niacin;
    about 5 IU to about 15 IU vitamin E; and
    a pharmaceutically acceptable excipient.

18. A method for treating, reducing the severity of, reducing the incidence of, or reducing the pathogenesis of type 2 diabetes in a subject in need thereof, comprising administering to the subject a pharmaceutical composition consisting of:
 about 0.5 mg to about 5 mg copper;
 about 25 mcg to about 200 mcg selenomethionine;
 about 50 mg to about 200 mg L-ascorbic acid;
 about 0.5 mg to about 5 mg pyridoxine;
 about 50 mcg to about 250 mcg biotin;
 about 50 mcg to about 250 mcg vitamin B12;
 about 100 µg to about 700 µg folic acid;
 about 5 mg to about 15 mg pantothenic acid;
 about 10 mg to about 30 mg niacin;
 about 5 IU to about 15 IU vitamin E; and
 a pharmaceutically acceptable excipient.

19. A method for treating, reducing the severity of, reducing the incidence of, or reducing the pathogenesis of type 2 diabetes in a subject in need thereof, comprising administering to the subject a pharmaceutical composition consisting of:
 about 45 mg to about 100 mg zinc;
 about 50 mg zinc;
 about 1.5 mg copper;
 about 100 mcg selenomethionine;
 about 120 mg L-ascorbic acid;
 about 2 mg pyridoxine;
 about 150 mcg biotin;
 about 150 mcg vitamin B12;
 about 400 µg folic acid;
 about 10 mg pantothenic acid;
 about 20 mg niacin;
 about 10 IU vitamin E; and
 a pharmaceutically acceptable excipient.

20. The method of claim 18, wherein the pharmaceutical composition consists of:
 about 50 mg zinc;
 about 1.5 mg copper;
 about 100 mcg selenomethionine;
 about 120 mg L-ascorbic acid;
 about 2 mg pyridoxine;
 about 150 mcg biotin;
 about 150 mcg vitamin B12;
 about 400 µg folic acid;
 about 10 mg pantothenic acid;
 about 20 mg niacin;
 about 10 IU vitamin E; and
 a pharmaceutically acceptable excipient.

* * * * *

UNITED STATES PATENT AND TRADEMARK OFFICE
CERTIFICATE OF CORRECTION

PATENT NO. : 11,452,742 B2
APPLICATION NO. : 16/463113
DATED : September 27, 2022
INVENTOR(S) : Ananda S. Prasad et al.

It is certified that error appears in the above-identified patent and that said Letters Patent is hereby corrected as shown below:

In the Claims

In Claim 18, Column 21, Lines 1-16:
"18. A method for treating, reducing the severity of, reducing the incidence of, or reducing the pathogenesis of type 2 diabetes in a subject in need thereof, comprising administering to the subject a pharmaceutical composition consisting of:
    about 0.5 mg to about 5 mg copper;
    about 25 mcg to about 200 mcg selenomethionine;
    about 50 mg to about 200 mg L-ascorbic acid;
    about 0.5 mg to about 5 mg pyridoxine;
    about 50 mcg to about 250 mcg biotin;
    about 50 mcg to about 250 mcg vitamin B12;
    about 100 µg to about 700 µg folic acid;
    about 5 mg to about 15 mg pantothenic acid;
    about 10 mg to about 30 mg niacin;
    about 5 IU to about 15 IU vitamin E; and
    a pharmaceutically acceptable excipient."

Should read:
--18. The method of claim 17, wherein the pharmaceutical composition consists of:
    about 50 mg zinc;
    about 1.5 mg copper;
    about 100 mcg selenomethionine;
    about 120 mg L-ascorbic acid;
    about 2 mg pyridoxine;
    about 150 mcg biotin;
    about 150 mcg vitamin B12;
    about 400 µg folic acid;
    about 10 mg pantothenic acid;
    about 20 mg niacin;

Signed and Sealed this
Twenty-second Day of November, 2022

Katherine Kelly Vidal
*Director of the United States Patent and Trademark Office* about 10 IU vitamin E; and
a pharmaceutically acceptable excipient.--.

In Claim 19, Column 21, Line 17 to Column 22, Line 9:
"19. A method for treating, reducing the severity of, reducing the incidence of, or reducing the pathogenesis of type 2 diabetes in a subject in need thereof, comprising administering to the subject a pharmaceutical composition consisting of:
about 45 mg to about 100 mg zinc;
about 50 zinc;
about 1.5 mg copper;
about 100 mcg selenomethionine;
about 120 mg L-ascorbic acid;
about 2 mg pyridoxine;
about 150 mcg biotin;
about 150 mcg vitamin B12;
about 400 µg folic acid;
about 10 mg pantothenic acid;
about 20 mg niacin;
about 10 IU vitamin E; and
a pharmaceutically acceptable excipient."

Should read:
--19. A method for treating, reducing the severity of, reducing the incidence of, or reducing the pathogenesis of type 2 diabetes in a subject in need thereof, comprising administering to the subject a pharmaceutical composition consisting of:
about 45 mg to about 100 mg zinc;
about 0.5 mg to about 5 mg copper;
about 25 mcg to about 200 mcg selenomethionine;
about 50 mg to about 200 mg L-ascorbic acid;
about 0.5 mg to about 5 mg pyridoxine;
about 50 mcg to about 250 mcg biotin;
about 50 mcg to about 250 mcg vitamin B12;
about 100 µg to about 700 µg folic acid;
about 5 mg to about 15 mg pantothenic acid;
about 10 mg to about 30 mg niacin;
about 5 IU to about 15 IU vitamin E; and
a pharmaceutically acceptable excipient.--.

In Claim 20, Column 22, Line 10:
"The method of claim 18,"

Should read:
--The method of claim 19,--.